United States Patent [19]

Schmidhalter

[11] Patent Number: 4,970,315
[45] Date of Patent: Nov. 13, 1990

[54] COPPER AND NICKEL DIHALIDE COMPLEXES, THEIR PREPARATION AND THE USE THEREOF

[75] Inventor: Beat Schmidhalter, Oberkirch, Switzerland

[73] Assignee: Ciba-Geigy Corporation, Ardsley, N.Y.

[21] Appl. No.: 385,759

[22] Filed: Jul. 26, 1989

[30] Foreign Application Priority Data

Jul. 28, 1988 [CH] Switzerland ............ 2868/88

[51] Int. Cl.$^5$ ............ C07D 453/02; G01N 31/22
[52] U.S. Cl. ............ 546/10; 544/225; 544/335; 544/336; 544/408; 544/409; 546/137
[58] Field of Search ............ 546/10; 544/225

[56] References Cited

U.S. PATENT DOCUMENTS

4,567,019  1/1986  Lawton ............ 422/57

FOREIGN PATENT DOCUMENTS

2951921  12/1979  Fed. Rep. of Germany .

OTHER PUBLICATIONS

Coffen et al., J. Org. Chem. 25, 503–5 (1970).
Bloomquist et al., Coord. Chem. Rev., vol. 47, pp. 125–133 (1982).
Long et al.; J. Chem. Soc. Dalton Transactions, pp. 762–765 (1975).
Browne, Australian J. Chem., vol. 25, No. 5, pp. 1809–1814 (1973).

*Primary Examiner*—Mark L. Berch
*Attorney, Agent, or Firm*—Michael W. Glynn

[57] ABSTRACT

Compounds of formula I

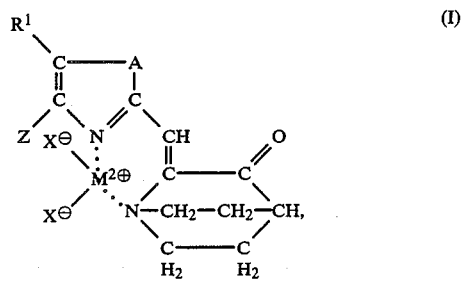

wherein
$X^\ominus$ is $Cl^\ominus$ or $Br^\ominus$,
M is $Cu^2{}_\oplus$ or $Ni^2{}_\oplus$,
Z is a halogen atom, $-NH_2$, $C_1-C_4$alkyl or $C_2-C_4$alkoxy,
$R^1$ is H, methyl methoxy, halogen or $-NH_2$, and
A is a group

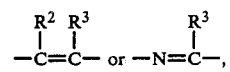

wherein $R^2$ and $R^3$ each independently have the same meaning as $R^1$.

The compounds are simultaneously cryochromic or thermochromic and are suitable as warning indicators for cooled or heated structural elements.

8 Claims, No Drawings

COPPER AND NICKEL DIHALIDE COMPLEXES, THEIR PREPARATION AND THE USE THEREOF

The present invention relates to copper(II) and nickel(II) dichloride and dibromide complexes of 2-(2'-pyridylmethylene)-3-quinuclidinones or 2-(2'-pyrimidylmethylene)-3-quinuclidinones which are substituted at least in 6-position, to said 3-quinuclidinones, to a process for the preparation of said complexes and to the use thereof as cryochromic and thermochromic warning indicators.

Thermochromic materials are used for the optical display of temperature changes which can trigger, for example, malfunctions in structural elements. For this purpose German Offenlegungsschrift No. 2,951,921 discloses a number of organic compounds which undergo a colour change upon decomposition. Reversible binary systems consisting of bis(p-aminophenyl)phthalides and organic acids are proposed for this utility in U.S. Pat. No. 4,567,019.

D. R. Bloomquist et al. describe in Coord. Chem. Rev. 47, p. 125–133 (1982), dichloro[2-(2'-quinonyl)-methylene-3-quinuclidinone]nickel(II), the yellow isomer of which is converted into a violet complex at 230° C. The original yellow colour can only be restored by cooling the violet complex to ca. −78° C. This nickel complex thus exhibits a pronounced thermal hysteresis, so that it is not suitable for use as a reverse system. It is further mentioned that the corresponding nickel dibromide complex and the 6'-methoxy derivative of the nickel dichloride complex do not exhibit thermochromism.

It has now been found that copper(II) dichloride and dibromide complexes and nickel(II) dichloride and dibromide complexes undergo two different colour changes at different temperatures if they contain a 6'-substituted 2-(2'-pyridyl)meihylene-3-quinuclidinone or 2-(2'-pyrimidyl)methylene-3quinuclidinone as complex ligand.

In one of its aspects, the invention relates to compounds of formula I $$\text{(I)}$$

wherein
$X^{\ominus}$ is $Cl^{\ominus}$ or $Br^{\ominus}$,
M is $Cu^{2\oplus}$ or $Ni^{2\oplus}$,
Z is a halogen atom, $-NH_2$, $C_1-C_4$alkyl or $C_2-C_4$alkoxy,
$R^1$ is H, methoxy, halogen or $-NH_2$, and
A is a group $$-\underset{|}{\overset{R^2}{C}}=\underset{|}{\overset{R^3}{C}}- \text{ or } -N=\underset{|}{\overset{R^3}{C}}-,$$

wherein $R^2$ and $R^3$ each independently have the same meaning as $R^1$.

The preferred meaning of $X^{\ominus}$ is $Cl^{\ominus}$.

Z as halogen is preferably fluoro, chloro or bromo. Z as alkyl and alkoxy may typically be methyl, ethyl, n-propyl, ispropyl, n-butyl, sec-butyl and tert-butyl and, respectively, methoxy, ethoxy, n-propoxy and isopropoxy, n-butoxy, sec-butoxy and tert-butoxy. The most preferred meaning of Z is methyl.

$R^1$ as halogen may be fluoro, chloro or bromo. The preferred meaning of $R^1$ is hydrogen.

A is preferably the group $$-\underset{|}{\overset{R^2}{C}}=\underset{|}{\overset{R^3}{C}},$$

in which $R^2$ and $R^3$ each independently have the same meaning as $R^1$. Most preferably $R^2$ and $R^3$ are each hydrogen.

A preferred embodiment of the compounds of formula I is the copper(II) dichloride complex of 2-[(6'-methyl-2-pyridyl)methylene]-3-quinuclidinone.

A further preferred embodiment of the compounds of formula I is the nickel(II) dichloride complex of 2-[(6'-methyl-2-pyridyl)methylene]-3-quinuclidinone.

The compounds of this invention may contain different amounts of water of crystallisation.

In another of its aspects, the present invention relates to a process for the preparation of compounds of formula I according to claim 1, which process comprises reacting a copper(II) dichloride or dibromide or a nickel(II) dichloride or dibromide with a compound of formula II $$\text{(II)}$$

wherein $R^1$, A and Z are as defined in claim 1.

The reaction is preferably carried out in alcoholic or aqueous-alcoholic solution. Examples of suitable alcohols are methanol, ethanol, n-propanol or isopropanol, n-butanol, sec-butanol or tert-butanol, pentanols and hexanols.

The reaction temperature may be in the range from 50° to 250° C., conveniently from 80° to 200° C.

The crystalline compounds of formula I precipitate from the cooled reaction mixture. They can be isolated by filtration and purified by conventional methods, for example by washing with a non-solvent or recrystallisation.

The compounds of formula II can be obtained in a manner which is known per se by condensation of at least 6-substituted pyridine- or pyrimidine-2-aldehydes of formula III

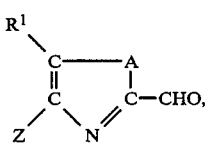

wherein A, Z and $R^1$ are as previously defined, with 3-quinuclidinone or salts threof, for example the hydrochlorides. The reaction is conveniently carried out in the presence of an alkali metal alcoholate. Examples of suitable alkali metals are Li, Na and K. The compounds of formula III are known or can be prepared by known methods.

In yet another of its aspects, the present invention relates to compounds of formula II

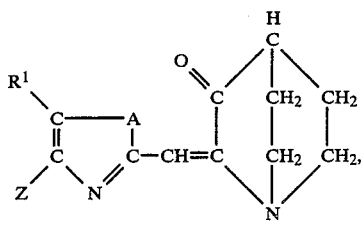

wherein

Z is a halogen atom, —$NH_2$, $C_1$–$C_4$alkyl or $C_1$–$C_4$alkoxy, $R^1$ is hydrogen, methyl, methoxy, halogen or —$NH_2$, and A is a group

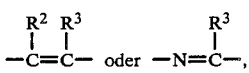

in which $R^2$ and $R^3$ each independently have the same meaning as $R^1$.

A, Z, $R^1$, $R^2$ and $R^3$ have the same preferred meanings as given for the compounds of formula I. A particularly preferred compound of formula I is 2-(6'-methyl-2'-pyridyl)methylene-3-quinuclidinone.

The compounds of formula I are coloured crystalline compounds which, surprisingly, undergo two reversible or irreversible colour changes at different temperatures. The colour change can take place even at low temperature, for example in the region of −190° C., so that low temperature applications are also encompassed, for example for the field of superconductors.

The compounds of formula I are suitable for use as warning and temperature indicators, for example for determining or preventing malfunctions of structural elements caused by changes or fluctuations in temperature (q.v. for example U.S. Pat. No. 4,567,019 and German Offenlegungsschrift No. 2 951 921). For this utility the compounds can be applied direct to an object and, if necessary, providsd with a protective layer. They can also be incorporated in a binder, for example of plastics material, or in plastics components.

The invention further relates to the use of compounds of formula I as cryochromic or thermochromic warning or temperature indicators.

The following Examples illustrate the invention in more detail.

(A) Preparation of starting materials
2-(6'-methyl-2'-pyridyl)methylene-3-quinuclidinone To a stirred solution of 1.74 g (0.075 mol) of sodium in 50 ml of absolute ethanol is added, over the course of 5 minutes, a mixture of 6.24 g (0.05 mol) of 6-methylpyridine-2-carbaldehyde and 8.08 g (0.05 mol) of 3-quinuclidinone hydrochloride in 125 mil of ethanol. With stirring, the yellow suspension is slowly heated to the boil and refluxed for 30 minutes. When the reaction is complete, the reaction mixture is cooled to room temperature and excess sodium ethanolate is destroyed with $H_2O$. The filtered solution is concentrated to half its volume and left to stand for crystallisation.

Yield: 10.2 g (89.5% of theory) of pale yellow crystals which melt at 108°–109° C.

Elemental analysis: 73.43% C, 7.14% H, 12.32% N, 7.06% O (theory: 73.66% C, 7.07% H, 12.27% N, 7.0% O).

(B) Preparatory Examples

Example 1

Cu(II) dichloride complex of 2-(6'-methyl-2'-pyridyl)methylene-3-quinuclidinone 1.14 g (0.05 mol) of 2-(6'-methyl-2'-pyridyl)methylene-3-quinuclidinone are dissolved in 100 ml of n-butanol and the solution is heated to reflux temperature. Then 0.28 g (0.05 mol) of $CuCl_2.2H_2O$ is dissolved in 12.5 ml of ethanol and the solution is heated to reflux temperature. This solution is then added to the first solution over 5 minutes. Upon completion of the addition, the reaction mixture is cooled to room temperature and the precipitated orange solid is isolated by filtration, washed thoroughly with hexane and dried at 80° C. under vacuum, affording 1.66 g (92.7% of theory) of orange crystals.

Elemental analysis: 46.30% C, 4.52% H, 7.87% N, 19.57% Cl, 17.5% Cu
(theory: 46.36% C, 4.45% H, 7.72% N, 19.55% Cl, 17.52% Cu, 4.41% O).

The product is recrystallised from absolute ethanol and a polymorphic pale green crystalline form is isolated. The different crystal modifications are detected by X-ray diffraction patterns. By dissolving the pale green form in n-butanol it is possible to recrystallise the orange form.

Example 2

Ni(II) dichloride complex of 2-(6'-methyl-2'-pyridyl)-methylene-3-quinuclidinone A hot solution of 2.28 g (0.01 mol) of nickel chloride 6.$H_2O$ in 25 ml of ethanol is added at reflux temperature to a stirred mixture of 2.28 g (0.01 mol) of 2-(6'-methyl-2'-pyridyl)methylene-3-quinuclidinone in 200 ml of n-butanol. The solvent is removed from the cooled reaction mixture under vacuum until a pale green Ni(II) complex precipitates. The solid is collected by filtration, washed thoroughly with hexane and then dried at 50° C. under vacuum.

Yield: 3.58 g (91.9% of theory) of the pale green complex.

Elemental analysis: 44.67% C, 4.92% H, 7.55% N, 18.80% Cl, 15.8% Ni (theory: 44.49% C, 4.87% H, 7.41% N, 18.76% Cl, 15.54% Ni, 8.93% O).

The compound contains 5.3% of water of crystallisation.

Example 3

Ni(II) dibromide complex of 2-(6'-chloro-2'-pyridyl)-methylene-3-quinuclidinone (a) 6-Chloropyridine-2-carbaldehyde is prepared in accordance with J. Chem. Commun., p. 410–411 (1974): 2.5 g (0.108 mol) of sodium are added, under argon, to 70 ml of absolute ethanol and dissolved with stirring. A suspension of 11.7 g (0.071 mol) of 3-quinuclidinone hydrochloride in 80 ml of absolute ethanol and 10 g (0.071 mol) of 6-chloropyridine-2-carbaldehyde in 100 ml of absolute ethanol is added, and the reaction mixture is heated for 30 minutes at reflux and then cooled to room temperature. The precipitated product is isolated by filtration, washed with water and dried, affording 1.72 g (89.6% of theory) of a yellowish crystalline substance which melts at 136° C.

(b) A hot solution of 1.11 g (0.05 mol) of NiB$_2$ in 12.5 ml of ethanol is added at reflux temperature to a stirred mixture of 1.24 g (0.05 mol) of 2-(6'-chloro-2'-pyridyl)-methylene-3-quinuclidinone in 100 ml of n-butanol. After cooling, the solvent is removed to half its volume and the crystalline product is collected by filtration, washed with n-hexane and dried at 70° C. under vacuum. Yield: 2.14 g (91.5% of theory) of a yellowish crystalline substance.

Elemental analysis: 33.5% C, 2.93% H, 6% N, 7.5% Cl, 33.68% Br, 12.5% Ni (theory: 33.42% C, 2.80% H, 6.00% N, 7.59% Cl, 34.20% Br, 12.57% Ni, 3.42% O). The compound contains 1.11% of water of crystallisation.

USE EXAMPLES

Example 4

The orange form of the copper complex of Example 1 is applied to a glass substrate and cooled. At −196° C. a reversible colour change to intsnse yellow occurs. Upon heating, an irreversible colour change to dark green occurs at 193° C.

Example 5

The pale green Ni complex is heated as described in Example 4. An irreversible colour change to intense yellow occurs at 119° C. An irreversible colour change to violet occurs at 160° C.

Example 6

The pale green Ni complex is heated as described in Example 4. A reversible colour change to dark yellow occurs at 140° C. A reversible colour change to golden yellow occurs at −196° C.

What is claimed is:

1. A compound of formula I

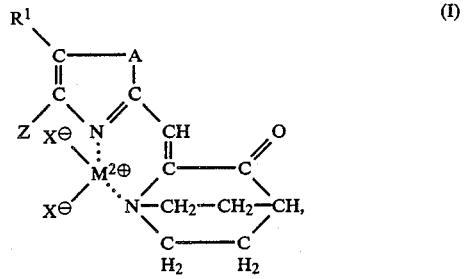

wherein
X$^\ominus$ is Cl$^\ominus$ or br$^\ominus$,
M is Cu$^{2\oplus}$ or Ni$^{2\oplus}$,
Z is a halogen atom, —NH$_2$, C$_1$–C$_4$alkyl or C$_2$–C$_4$alkyl,
R$^1$ is H, methoxy, halogen or —NH$_2$, and
A is a group

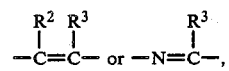

wherein R$^2$ and R$^3$ each independently have the same meaning as R$^1$.

2. A compound of formula I according to claim 1, wherein X$^\ominus$ is Cl$^\ominus$.

3. A compound of formula I according to claim 1, wherein Z is methyl.

4. A compound of formula I according to claim 1, wherein R is hydrogen.

5. A compound of formula I according to claim 1, wherein A is the group

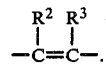

6. A compound of formula I according to claim 1, wherein R$^2$ and R$^3$ are each hydrogen.

7. A compound of formula I according to claim 1, which is the copper(II) dichloride complex of 2-[(6'-methyl-2'-pyridyl)methylene]-3-quinuclidinone.

8. A compound of formula I according to claim 1, which is the nickel(II) dichloride complex of 2-[(6'-methyl-2'-pyridyl)methylene]-3-quinuclidinone.

* * * * *